(12) United States Patent
Boese et al.

(10) Patent No.: US 6,992,213 B2
(45) Date of Patent: Jan. 31, 2006

(54) METHOD FOR REMOVING TRIFLUOROETHANOL FROM LIQUIDS

(75) Inventors: Olaf Boese, Hannover (DE); Katja Peterkord, Hannover (DE)

(73) Assignee: Solvay Fluor und Derivate GmbH, Hannover (DE)

( * ) Notice: Subject to any disclaimer, the term of this patent is extended or adjusted under 35 U.S.C. 154(b) by 91 days.

(21) Appl. No.: 10/791,271

(22) Filed: Mar. 3, 2004

(65) Prior Publication Data

US 2004/0232082 A1 Nov. 25, 2004

Related U.S. Application Data

(63) Continuation of application No. PCT/EP02/09546, filed on Aug. 27, 2002.

(30) Foreign Application Priority Data

Sep. 4, 2001 (DE) ................ 101 43 170

(51) Int. Cl.
 *C07C 67/48* (2006.01)

(52) U.S. Cl. ............ 560/248; 560/227; 568/840; 568/841; 568/842; 568/868

(58) Field of Classification Search ............ 560/248, 560/129; 210/656, 768, 807; 568/840, 841, 568/842, 868
See application file for complete search history.

(56) References Cited

U.S. PATENT DOCUMENTS

| 3,335,173 | A | * | 8/1967 | Anello | .................. 560/227 |
| 4,859,793 | A | | 8/1989 | Hurtel | |
| 5,763,684 | A | * | 6/1998 | Kawai et al. | ............ 568/682 |
| 6,107,529 | A | | 8/2000 | Shields | |

FOREIGN PATENT DOCUMENTS

| EP | 0696077 | | 2/1996 |
| EP | 835858 | | 4/1998 |
| JP | 62056446 | * | 3/1987 |
| JP | 4308537 | | 10/1992 |

* cited by examiner

*Primary Examiner*—Johann Richter
*Assistant Examiner*—Karl Puttlitz
(74) *Attorney, Agent, or Firm*—Crowell & Moring LLP

(57) ABSTRACT

Trifluoroethanol can be isolated from organic liquids that are contaminated by trifluoroethanol by bringing the contaminated liquid into contact with a molecular sieve having a pore size ranging between 0.5 and 1.0 nm, e.g., with molecular sieve 13X. This enables, for example, trifluoroacetic acid trifluoroethyl esters, bis(trifluoroethyl)carbonate or trifluoroethyl esters of phosphoric, phosphonic or phosphinic acid to be purified.

7 Claims, No Drawings

METHOD FOR REMOVING TRIFLUOROETHANOL FROM LIQUIDS

CROSS REFERENCE TO RELATED APPLICATIONS

This application is a continuation of international patent application no. PCT/EP02/09546, filed Aug. 27, 2002 designating the United States of America and published in German as WO 03/020419, the entire disclosure of which is incorporated herein by reference. Priority is claimed based on Federal Republic of Germany patent application no. DE 101 43 170.8, filed Sep. 4, 2001.

BACKGROUND OF THE INVENTION

The invention relates to a method for removing trifluoroethanol from organic liquids.

Trifluoroethanol can be used as a solvent. It can also be used as a building block in chemical synthesis, such as the synthesis of esters, which can then be used, in turn, as solvents or as building blocks in syntheses. Organic liquids may therefore contain trifluoroethanol for example, as a result of the synthesis condition or as a consequence of decomposition reactions. In industry, it is frequently difficult to remove the trifluoroethanol. For example, the content may be very low, so that losses in yield of the organic liquid arise during a distillation. With some organic liquids, such as trifluoroethyl trifluoroacetate, trifluoroethanol forms an azeotrope and can therefore not be removed at all by distillation.

SUMMARY OF THE INVENTION

It is an object of the present invention to provide a improved method for removing trifluoroethanol from liquids.

Another object of the invention is to provide a simple and effective method for removing trifluoroethanol (2,2,2-trifluoroethanol) from organic liquids.

These and other objects are achieved in accordance with the present invention by providing a method for removing trifluoroethanol from an organic liquid which is contaminated with trifluoroethanol, said method comprising contacting the contaminated organic liquid with a molecular sieve having a pore size of 0.5 to 1 nm.

In accordance with the method of the invention for removing trifluoroethanol from organic liquids, which are contaminated with trifluoroethanol, the contaminated organic liquids are contacted with a molecular sieve having a pore size of 0.5 to 1 nm.

In principle, the method of the invention can be used for any organic liquid, the pressure employed usually not playing a role. Of course, it is advantageous to carry out the method at ambient pressure. Persons skilled in the art can easily determine whether the inventive method functions when applied to a particular organic liquid. It is only necessary to take a sample after a period of, for example, one or two hours and check by gas chromatography whether the content of trifluoroethanol has been decreased.

Preferably, the method of the invention is used for ethers and particularly for esters of trifluoroethanol, which are contaminated with trifluoroethanol. Preferably, trifluoroethanol is removed from esters of carbonic acid or carboxylic acids, which are contaminated with trifluoroethanol. Likewise, it is possible using the method of the invention to purify phosphate esters or phosphonate esters, which have been esterified with trifluoroethanol, such as the tris(trifluoroethyl) phosphates or the phosponate esters and phosphinate esters, which are described in U.S. Pat. No. 6,210,840. The phosphonic and phosphinic acids, which are described in this last mentioned U.S. patent, contain alkyl, halogenalkyl, aryl, aralkyl, or $CH_2CO(O)OR$ groups, which are liked directly to phosphorus. In this case, the R group is, for example, alkyl or halogenated alkyl.

Preferred carboxylate esters, which are purified pursuant to the invention, include esters of acetic acid, propionic acid, butanecarboxylic acid, pentanecarboxylic acid, hexanecarboxylic acid and heptanecarboxylic acid. The aforementioned esters may be substituted, for example, by halogen atoms, preferably by at least one fluorine atom, or other substituents, such as C1–C4 alkoxy groups. Especially preferred is purification of trifluoroethyl, esters of carbonic acid, trifluoroacetic acid, perfluoropropionic acid or trifluorobutanoic acid.

A molecular sieve which has a pore size of 0.85 nm is particularly preferred as molecular sieve for use in the present invention.

Advantageously, the removal of trifluoroethanol is carried out at ambient temperature. However, if desired, it is also possible to work at lower temperatures, such as temperatures down to 0° C. or lower, or also at higher temperatures, up to the boiling point of the organic liquid or of trifluoroethanol.

The method of the invention has the following advantages:

The invention makes it possible to achieve anhydrous removal of trifluoroethanol from organic liquids and solvents without requiring separation by distillation. The molecular sieve can be removed by decanting or filtering. The method is applicable over a wide range of concentrations. The organic liquid, which is to be purified, is not contaminated. Since the addition of water is not necessary, the method can also be employed with substances which are likely to hydrolyze in the presence of water.

The method of the invention is particularly suitable when solvents of high purity are required in electrotechnology, for example, as an electrolyte solvent for lithium ion batteries or for double layer capacitors.

EXAMPLES

The following examples are intended to illustrate and explain the invention in further detail without limiting its scope.

Example 1

Purification of Trifluoroethyl Trifluoroacetate

Because it forms an azeotrope, trifluoroethanol could not be removed by distillation from trifluoroethyl trifluoroacetate. In order to remove the trifluoroethanol (0.479 area percent, GC) from trifluoroethyl trifluoroacetate (10 g, 196 g/mole, 0.051 moles), samples of contaminated trifluoroethyl trifluoroacetate were each contacted with one gram of a respective molecular sieve. The resulting contents of trifluoroethanol after the treatment are listed in the following Table 1:

TABLE 1

Trifluoroethanol contents (GC, area percent) in trifluoroethyl trifluoroacetate after treatment with different molecular sieves.

| Example | Molecular Sieve Used | Contact time: 1 hour TFE content (area %) | Contact time: 10 hours TFE content (area %) |
|---|---|---|---|
| 1.1 | Molecular sieve 4A | 0.455 | 0.435 |
| 1.2 | Molecular sieve 5A | 0.377 | 0.100 |
| 1.3 | Molecular sieve 13X | 0.205 | 0.021 |

Example 2

Purification of Bis(trifluorethyl) Carbonate

Bis(trifluorethyl) carbonate (10 grams, 226 g/mole, 0.044 moles) containing 2.47% of trifluoroethanol (GC, area %) was contacted with 1 gram of molecular sieve 13X. The trifluoroethanol content was 0.82% after 2 hours and 0.27% after 12 hours.

The examples show that the molecular sieve 13X is particularly suitable for removing 2,2,2-trifluoroethanol.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A method for removing trifluoroethanol from an organic liquid which is contaminated with trifluoroethanol, said method comprising contacting the contaminated organic liquid with a molecular sieve having a pore size of 0.5 to 1 nm.

2. A method according to claim 1, wherein said contaminated organic liquid comprises an ester of trifluoroethanol which is contaminated with trifluoroethanol.

3. A method according to claim 2, wherein said ester of trifluoroethanol contaminated with trifluoroethanol is an ester of an acid selected from the group consisting of carbonic acid, carboxylic acids, phosphoric acid, phosphonic acid and phosphinic acid.

4. A method according to claim 2, wherein said ester of trifluoroethanol contaminated with trifluoroethanol is selected from the group consisting of esters of acetic acid, propionic acid and butanecarboxylic acid.

5. A method according to claim 2, wherein said ester of trifluoroethanol contaminated with trifluoroethanol is selected from the group consisting of esters of acetic acid, propionic acid and butanecarboxylic acid substituted by at least one fluorine atom.

6. A method according to claim 1, wherein said organic liquid which is contaminated with trifluoroethanol comprises an ester of carbonic acid, trifluoroacetic acid, pentafluoropropionic acid or heptafluorobutanoic acid.

7. A method according to claim 1, wherein said molecular sieve is molecular sieve 13X having a pore size of 0.85 nm.

* * * * *